US006833786B1

(12) United States Patent
Sun et al.

(10) Patent No.: US 6,833,786 B1
(45) Date of Patent: Dec. 21, 2004

(54) PNEUMATIC DEMULTIPLEXER FOR CONTROLLING MULTIPLE ASSISTIVE TECHNOLOGY DEVICES

(75) Inventors: Ying Sun, Wakefield, RI (US); Kaylen J. Haley, West Kingston, RI (US); Kerri-Anne Lachance, Coventry, RI (US); Kerri Pinnock, Little Compton, RI (US)

(73) Assignee: The Board of Governors for Higher Education, State of Rhode Island and Providence Plantations, Providence, RI (US)

( * ) Notice: Subject to any disclaimer, the term of this patent is extended or adjusted under 35 U.S.C. 154(b) by 187 days.

(21) Appl. No.: 10/314,457

(22) Filed: Dec. 6, 2002

Related U.S. Application Data

(60) Provisional application No. 60/338,108, filed on Dec. 6, 2001.

(51) Int. Cl.[7] .............................. G08B 1/08; H04Q 7/00
(52) U.S. Cl. ............. 340/539.12; 340/506; 340/825.19; 341/21
(58) Field of Search ................... 340/825.19, 505, 340/506, 539.12; 341/21

(56) References Cited

U.S. PATENT DOCUMENTS

| | | | |
|---|---|---|---|
| 4,567,479 A | | 1/1986 | Boyd |
| 4,746,913 A | * | 5/1988 | Volta ........................... 345/184 |
| 4,865,610 A | | 9/1989 | Muller |
| 5,126,731 A | | 6/1992 | Cromer et al. |
| 5,172,147 A | * | 12/1992 | Rockhill ....................... 396/428 |
| 5,365,026 A | | 11/1994 | Cromer et al. |
| 5,600,311 A | | 2/1997 | Rice et al. |
| 5,815,147 A | * | 9/1998 | Bogen et al. ................ 345/835 |

FOREIGN PATENT DOCUMENTS

GB  2137001 A  *  9/1984

* cited by examiner

Primary Examiner—Daniel J. Wu
Assistant Examiner—Samuel J. Walk
(74) Attorney, Agent, or Firm—Gauthier & Connors LLP

(57) ABSTRACT

A pneumatic demultiplexer that allows a person with a disability to control multiple assistive technology devices by the use of a single sip-and-puff tube. The devices to be controlled are operated by a single pneumatic or electrical switch input. The pneumatic demultiplexer is under the control of a microprocessor. In a scan stage the user selects the target device via scrolling LED indicators. When a specific device is chosen, the corresponding solenoid valve is activated to connect the input sip-and-puff port to the pneumatic output port. In the activation stage, the input sip-and-puff tube controls the target device directly via the pneumatic demultiplexer. The microprocessor monitors the line activity via a sip-or-puff switch. A watchdog timer is implemented by the microprocessor. After there is a lack of activity for preprogrammed time period, the system switches from the activation stage back to the scan stage.

7 Claims, 4 Drawing Sheets

PNEUMATIC DEMULTIPLEXER FOR CONTROLLING MULTIPLE ASSISTIVE TECHNOLOGY DEVICES

PRIORITY DATA

This application claims the benefit of U.S. Provisional Application No. 60/338,108. filed Dec. 6, 2001, and hereby incorporated by reference.

BACKGROUND OF THE INVENTION

The present invention relates to the field of assistive devices for disabled people, and in particular to devices that enable the user thereof to selectively apply a pneumatic signal to multiple assistive technology appliances.

According to the latest reports from the National Center for Health Statistics, 13.6 million Americans have limited use of their hands and 7.4 million Americans use assistive technology devices to accommodate mobility impairments. For severe cases of mobility impairments such as quadriplegia and cerebral palsy a sip-and-puff system provides a reliable mechanism for controlling assistive technology devices. The sip-and-puff system uses a breathing tube to produce one or more switching signals. For example, a system that differentiates soft sip, soft puff, hard sip, and hard puff can produce four switching signals, which are sufficient for controlling sophisticated devices such as a powered wheelchair.

A problem arises when a person uses more than one assistive technology device and each device has its own sip-and-puff control. Multiple sip-and-puff tubes are difficult to position and result in congestion in front of the user's face. Prior art has addressed this problem to a certain extent by use of four separate inline tubes attached to and supported by a single arm (Quad Puff System or Quad Sip System, Enabling Devices, www.enablingdevices.com). However, a person who has limited head and neck mobility may have difficulty reaching all four tubes. The congestion problem still remains because the multiple inline tubes block a significant portion of the person's view.

U.S. Pat. No. 5,600,311 describes an environmental control system for the severely disabled that has an auxiliary pass-though port. A single switch controls the environmental control system by use of the sequential scanning method described above. When the auxiliary pass-though port is selected, the system suspends the scanning and enters the pass-through mode. In the pass-though mode the input switch closures are passed to the target device connected to the auxiliary port. The pass-though mode is exited by a long depression of the switch for a preprogrammed time period. However, this pass-through method is only for an electrically-controlled switch. It does not solve the problem of controlling a device that requires a plurality of different actions from a sip-and-puff tube. The long depression of the switch as the exit signal may also impose a limitation on operating a device that requires closings the switch for long periods of time.

The present invention addresses the aforementioned drawbacks.

SUMMARY OF THE INVENTION

Broadly, the invention comprises an apparatus for controlling a plurality of assistive technology devices that includes a manifold comprising a pneumatic input port, a first pneumatic output adapted to communicate with a first assistive technology device and a second pneumatic output adapted to communicate with a second assistive technology device. The first pneumatic output is in communication with a first solenoid valve operative to close and open the first pneumatic output port. The second pneumatic output port is in communication with a second solenoid valve operative to close and open the second pneumatic output port.

Means for controlling the opening of either the first or second solenoid valve are actuated by the passage of a pneumatic signal through said input port. When the first pneumatic valve is opened the input port and the first output port are in communication, the second pneumatic valve being closed, to create a first pneumatic flowpath from the input port to the first output port to allow the input port to communicate with the first assistive technology device. When the second pneumatic valve is open the input port and the second output port are in communication, said first pneumatic valve being closed, to create second pneumatic flow path to allow the input port to communicate with the second assistive technology device. Means for determining when the application of the pneumatic signal will actuate the means for controlling to open either said first solenoid valve or said second solenoid valve.

In another aspect, the invention includes a pneumatic demultiplexer that allows a person with a disability to control multiple assistive technology devices by the use of a single sip-and-puff tube. The devices to be controlled are operated by a single pneumatic or electrical switch input. The pneumatic demultiplexer is under the control of a microprocessor. In a scan stage the user selects the target device via scrolling LED indicators. When a specific device is chosen, a corresponding solenoid valve is activated to connect the input sip-and-puff port to the pneumatic output port. In the activation stage, the input sip-and-puff tube controls the target device directly via the pneumatic demultiplexer. The microprocessor monitors the line activity via a sip-or-puff switch. A timer is implemented by the microprocessor. After there is a lack of activity for a pre-programmed time period, the system switches from the activation stage back to the scan stage.

In yet another aspect, the invention includes a pneumatic demultiplexer that allows the use of a single sip-and-puff tube to control a plurality of devices that are operated by electrical and/or pneumatic switches.

These and other objects, features and advantages of the present invention will become more apparent in light of the following detailed description of the preferred embodiments thereof, as illustrated in the accompanying drawings.

DETAILED DESCRIPTION OF THE INVENTION

Figure 1:
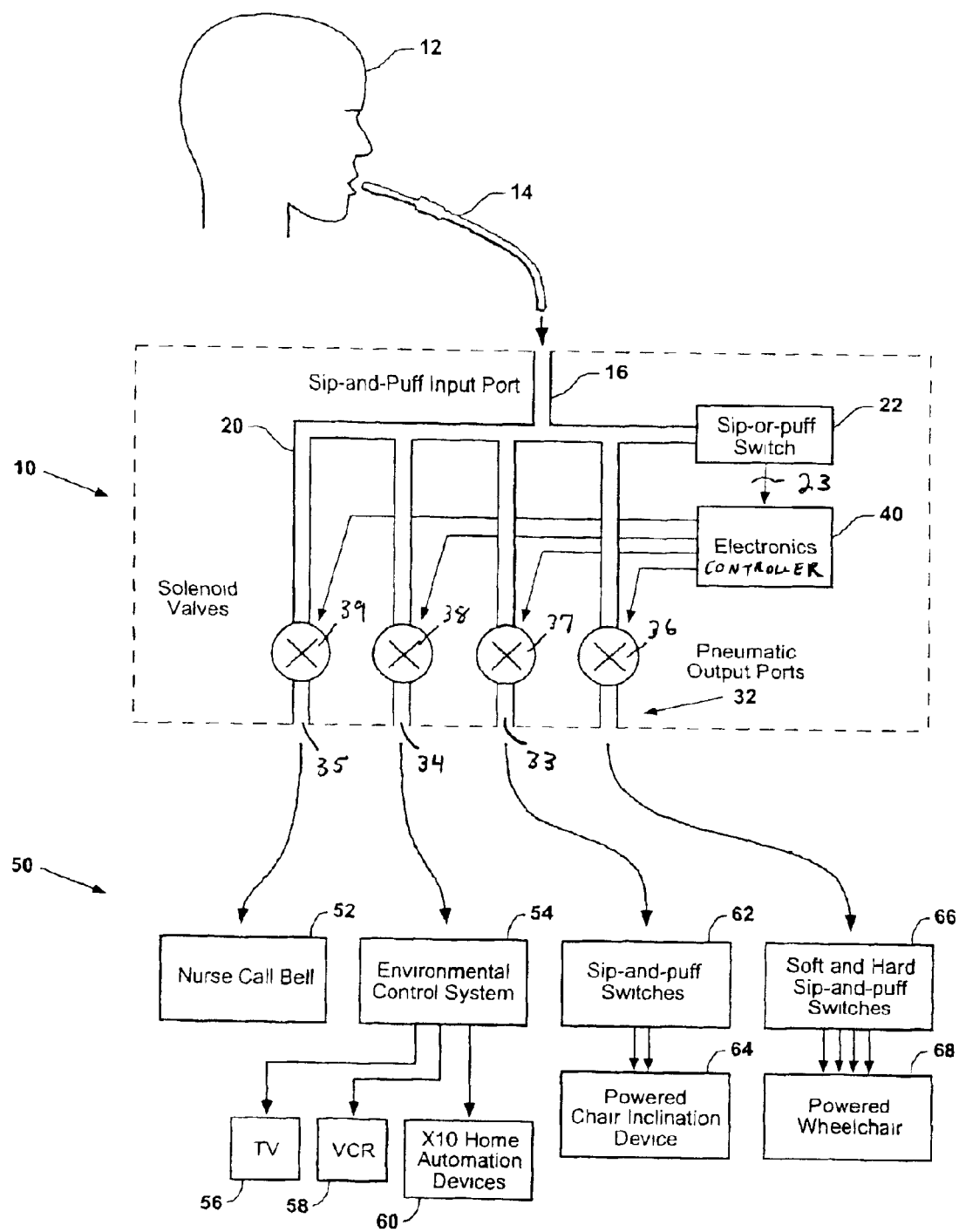
FIG. 1 is a schematic diagram of an embodiment of the invention and its application.

FIG. 1 is a block diagram illustration of a pneumatic demultiplexer 10 and a plurality of target assistive technology devices 50. A user 12 sends a pneumatic signal via a sip-and-puff tube 14, which is connected to an input port 16 of the pneumatic demultiplexer 10. Inside the pneumatic demultiplexer a manifold 20 connects the input port 16 to a plurality of pneumatic output ports 32–35 via a set of open/close valves 36–39, (e.g., solenoid valves). The embodiment in FIG. 1 shows four pneumatic output ports, which can be varied in number depending on the application requirement. Each of the solenoid valves 36–39 is a two-connector on-off valve which it is normally off (i.e., closed) and turned on at an appropriate time by an electronic controller 40. The electronic controller 40 sequentially and repetitively scans through all output ports. The user selects a specific pneumatic port by either sipping or puffing. A sip-or-puff switch 22 converts the pneumatic signal from the user to an electrical signal on a line 23, which is sent to the electronic controller 40. The plurality of pneumatic ports 32–35 allow the user to control a plurality of assistive technology devices 50. The embodiment in FIG. 1 shows four assistive technology devices that have different levels of complexity in their switching mechanisms. A nurse call bell system 52 requires a simple toggle switch (not shown). An environmental control system 54 sequentially scans through toggle switches (not shown) that control a TV 56, VCR 58, and X10 home automation devices 60. A powered chair inclination device 64 includes a sip switch and a puff switch 62 to control the chair inclination, (e.g., forward and backward). Finally, a powered wheelchair 68 requires four electrical signals to operate. The pneumatic signal from the output port 32 is input to sip and puff switch 66, what decodes the pneumatic signal provided to the powered wheelchair four electrical signals. The nurse call bell and the environmental control system receive electrical signals from the pneumatic demultiplexer, while the sip and puff switches 62, 66 received pneumatic signals from the pneumatic demultiplexer.

Figure 2:
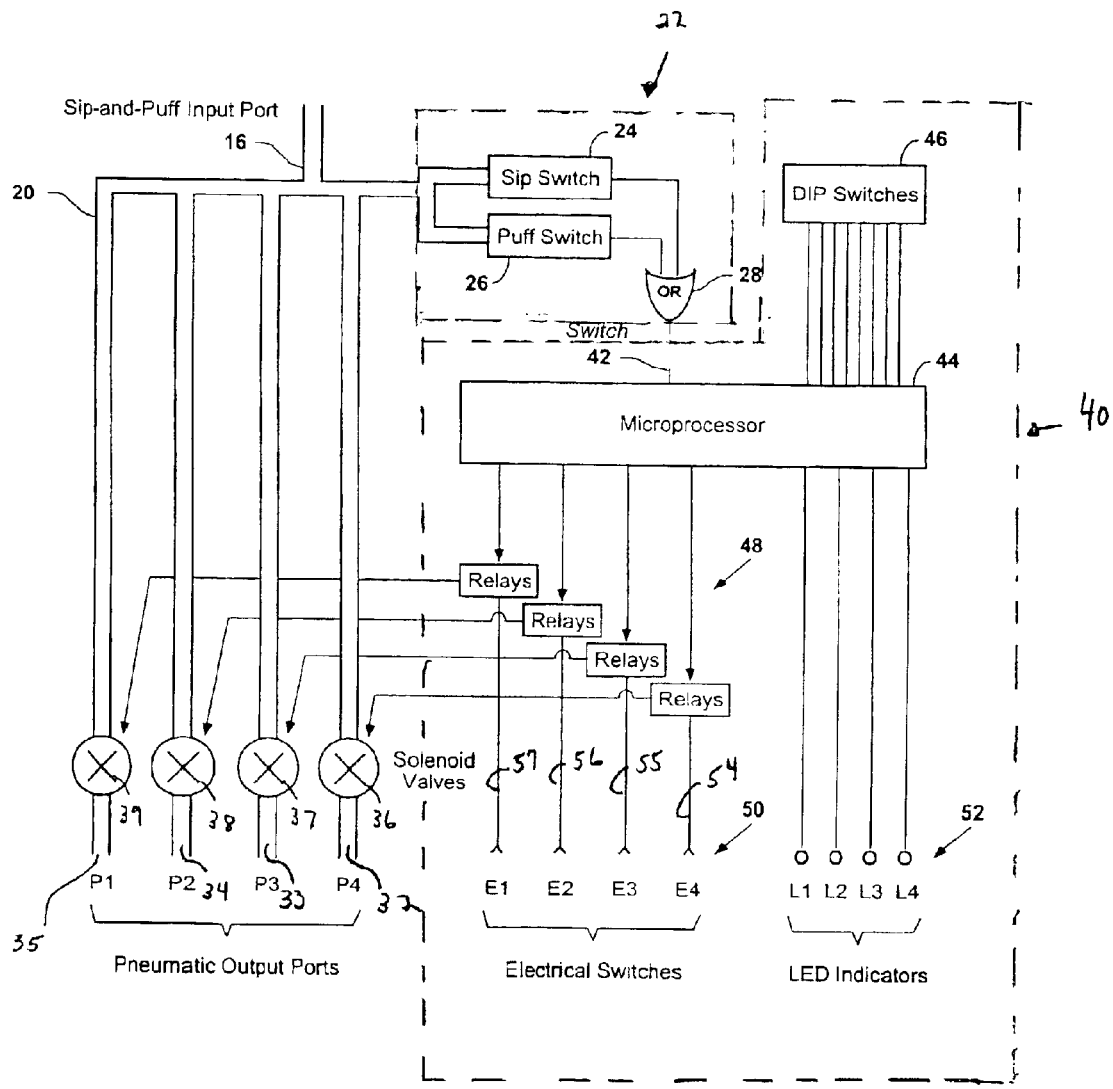
FIG. 2 is a detailed block diagram of an embodiment of the invention.

FIG. 2 is a detailed block diagram of an embodiment of the invention is shown. The system contains pneumatic components as well as electronic components. For the pneumatic part, the sip-and-puff input port 16 is demultiplexed into four pneumatic output ports 32–35 via the four normally closed solenoid valves 36–39. The pneumatic signal from the user is decoded by use a sip switch 24 and a puff switch 26. The signals from the sip switch and the puff switch are combined together via an OR gate 28, resulting in an output signal Switch on a line 42. For the electronic part, the electrical controller 40 includes an embedded microprocessor 44, which controls the operation of the system. The system operates in two modes: SCAN and ACTIVATION. In the SCAN mode, all solenoid valves 36–39 are closed. The microprocessor 44 scans through the choices of the output port by turning on the corresponding light emitting diode (LED) 52 one at a time. When Switch signal on the line 42 is asserted, the microprocessor opens the solenoid valve that corresponds to the lit LED. All other solenoid valves remain closed. Once a device is selected in the SCAN mode, the system enters the ACTIVATION mode. In the ACTIVATION mode, the input sip-and-puff port 16 is connected to the chosen pneumatic output port. The pneumatic demultiplexer 10 becomes transparent in the sense that the user has an airway directly connected to the target assistive technology device. As long as the system is in the ACTIVATION mode, the user can continue to send pneumatic signals to the target device. The return from the ACTIVATION mode back to the SCAN stage is accomplished by use of a watchdog timer implemented inside the microprocessor. During the ACTIVATION mode the microprocessor constantly monitors the Switch signal on the line 42 that indicates activity on the pneumatic line. When there is a lack of activity for a preprogrammed time period, the system returns to the SCAN mode.

Dual-in-line (DIP) switches 46 are used to program certain system parameters such as the number of output ports to be scanned and the time period for the watchdog timer.

The microprocessor 44 provides control signals to relays 48a–48d to control the solenoid valves 36–39, respectively. The relays 48a–48d also provide electrical switch outputs 54–57 corresponding to the pneumatic outputs 32–35. For assistive technology devices that use electrical switches, the electrical switch outputs can be used instead of the pneumatic outputs. The design of the relay assembly is described as follows.

Figure 3:
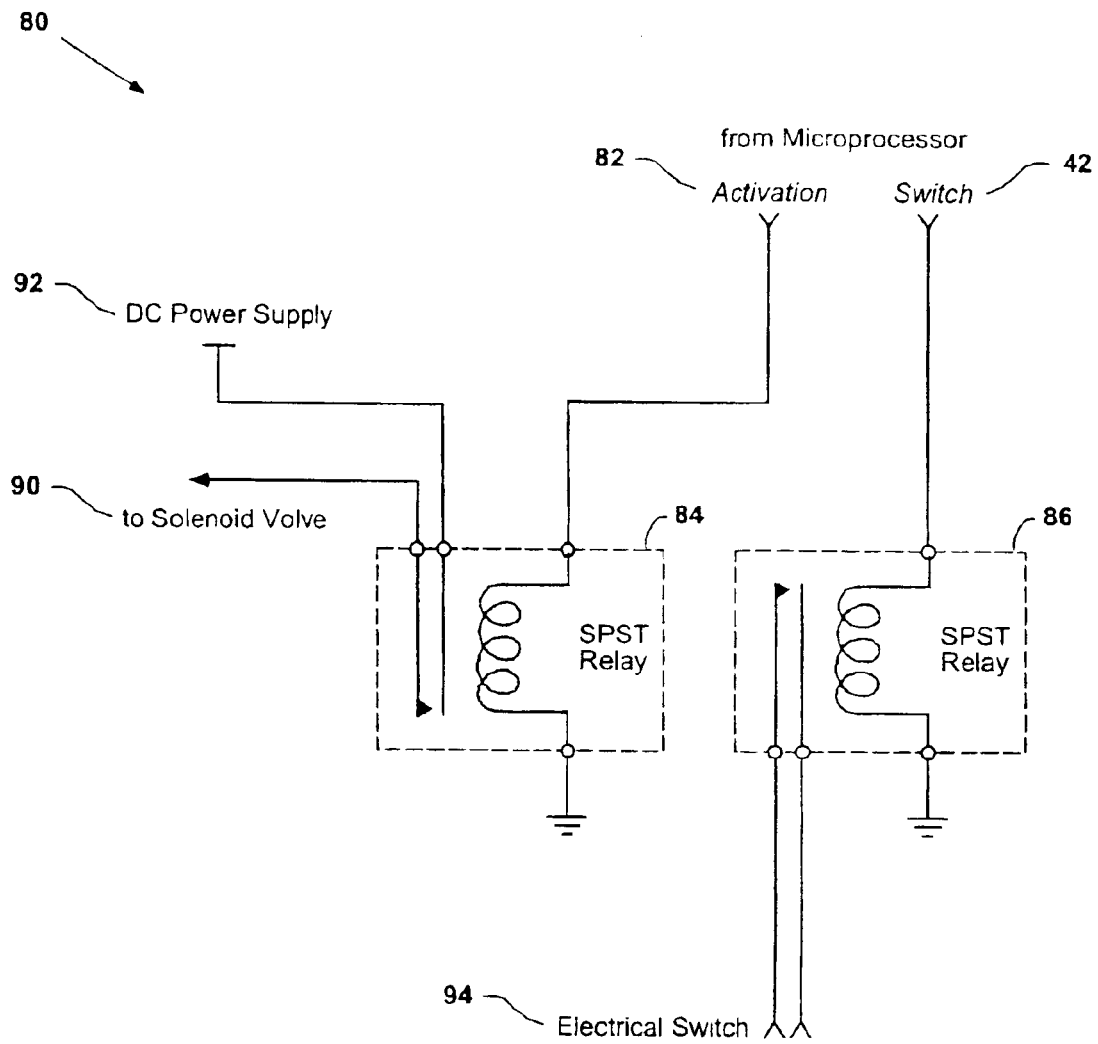
FIG. 3 is a schematic diagram of the relay assembly.

Referring to FIG. 3, two single-pole-single-throw (SPST) relays 80 are used for each of the four output ports. The microprocessor 44 (FIG. 2) sends an Activation signal on a line 82 to relay 84. The closure of relay 84 allows the DC power supply 92 to energize the chosen solenoid value 90. The Activation signal on the line 82 remains asserted during the ACTIVATION mode, resulting in a direct connection of the airway from the input sip-and-puff port 16 (FIG. 2) to the chosen pneumatic output port. In the meantime, the Switch signal on the line 42 (FIG. 2) controls a second SPST relay 86. The closures of the Switch signal on the line 42 are passed on to the electrical switch output 94, which can be used to control an electrical-switch-operated device.

Figure 4:
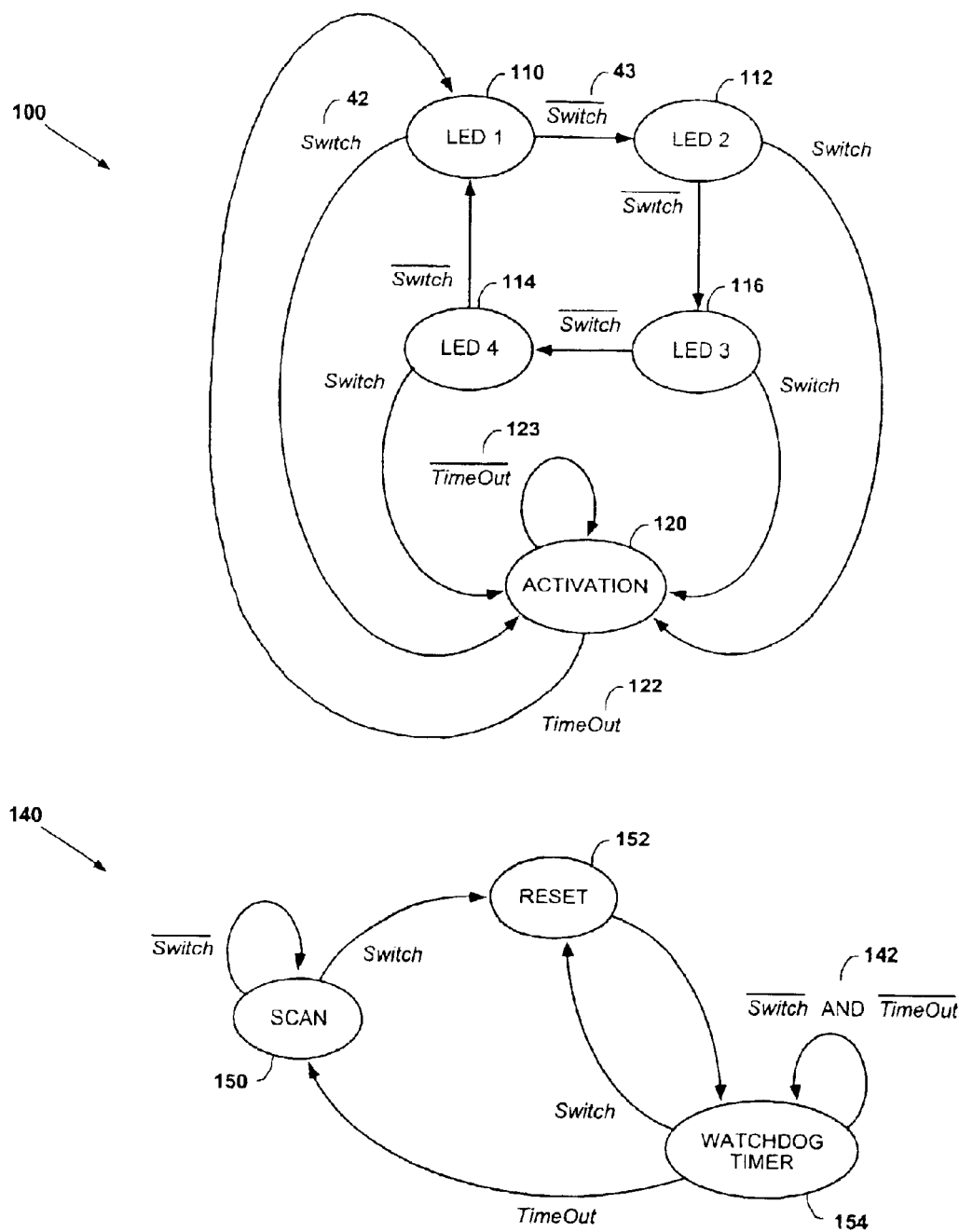
FIG. 4 is a state diagram of an embodiment of the invention.

Referring to FIG. 4, the state diagram for the operation of an embodiment of the invention 100 is shown. In the SCAN mode, the system cycles though the four states: LED1 110, LED2 112, LED3 114, and LED4 116, when the Switch signal on the line 42 (FIG.2) is negated. In FIG. 4, Not-Switch is indicated by overbar-Switch 43. When Switch 42 is asserted in any of the four scanning states, the system moves to the ACTIVATION mode 120. Depending on which LED is chosen the corresponding pneumatic output port is activated as described previously. The watchdog timer is also activated. The watchdog timer asserts the TimeOut signal 122 when the timer expires. The system remains in the ACTIVATE state when Not-Time out 123 is true, returns to the SCAN stage when Time out 122 is true.

A separate state diagram 140 depicts the operation of the watchdog timer. The system remains in the SCAN state 150 when Not-Switch is true. When Switch is asserted, the system enters the RESET state 152 and resets the timer. Immediately after the RESET state the system enters the WATCHDOG TIMER state 154 and starts the watchdog timer. The watchdog timer continues to tick when both Not-Switch and Not-Time out 142 are true. If there is activity on the pneumatic line, Switch is asserted and the system moves to the RESET state to restart the watchdog timer. If there is no activity on the pneumatic line for a preprogrammed time period, the watchdog timer expires and Time out is asserted. The assertion of Time out brings the system from the WATCHDOG TIMER state 154 back to the SCAN state 150.

Although the present invention has been shown and described with a preferred embodiment thereof, various changes, omissions and additions to the form and detail thereof, may be made therein, without departing from the spirit and scope of the invention.

What is claimed is:

1. An apparatus for controlling a plurality of assistive technology devices, said apparatus comprises:
   a manifold comprising one pneumatic input port;
   a first pneumatic output adapted to communicate with a first assistive technology device;
   a second pneumatic output adapted to communicate with a second assistive technology device, said first pneumatic output in communication with a first solenoid valve operative to close and open said first pneumatic output port; said second pneumatic output port in communication with a second solenoid valve operative to close and open said second pneumatic output port;

means for controlling the opening of either said first or second solenoid valve, said means for controlling being actuated by the passage of a pneumatic signal through said input port, whereby when said first pneumatic valve is opened said input port and said first output port are in communication, said second pneumatic valve being closed, thereby creating a first pneumatic flow-path from said input port to said first output port to allow said input port to communicate with said first assistive technology device and when said second pneumatic valve is open said input port and said second output port are in communication, said first pneumatic valve being closed, thereby creating a second pneumatic flow path to allow said input port to communicate with said second assistive technology device; and means for determining when the application of said pneumatic signal will actuate the means for controlling to open either said first solenoid valve or said second solenoid valve.

2. The apparatus of claim 1 wherein the means for controlling comprises a sip-and-puff switch that receives said pneumatic signal and provides an electric signal indicative thereof and a microprocessor that receives said electric signal.

3. The apparatus of claim 2 wherein the means for determining comprises a first indicator and a second indicator in communication with said microprocessor, said first indicator and said second indicator outputting a first display when said first solenoid valve and said second solenoid valve are closed, a second display when said first solenoid valve is open and said second solenoid valve is closed and a third display when said second solenoid valve is open and said first solenoid valve is closed, said microprocessor providing a control signal based on the which display is outputted when said electric signal is received; said control signal opening said first solenoid valve when said pneumatic signal is received by said sip-and-puff switch when said first and said second indicators output said second display and said control signal opening said second solenoid valve when said pneumatic signal is received by said sip-and-puff switch when said first and second indicators output said third display.

4. The apparatus of claim 3 wherein the means for controlling further comprises:
　a first electrical switch output, said first electrical switch output being activated when said first solenoid valve is opened; and
　a second electrical switch output, said second electrical switch output being activated when said second solenoid valve is opened.

5. The apparatus of claim 3 which further comprises:
　means for timing the duration of the output of said first display.

6. The apparatus of claim 5 which further comprises:
　means for timing the duration of the output of said second and third displays.

7. The apparatus of claim 4 wherein said first electrical switch output is adapted to communicate with a third assistive technology device and said second electrical output is adapted to communicate with a fourth assistive technology device.

* * * * *